United States Patent [19]

Braun et al.

[11] Patent Number: 4,855,423

[45] Date of Patent: Aug. 8, 1989

[54] PREPARATION OF SULFATOBETAINES

[75] Inventors: Gerold Braun, Ludwigshafen; Chung-Ji Tschang, Bad Durkheim; Christos Vamvakaris, Kallstadt; Klaus Glaser, Mutterstadt, all of Fed. Rep. of Germany

[73] Assignee: BASF Aktiengesellschaft, Ludwigshafen, Fed. Rep. of Germany

[21] Appl. No.: 106,802

[22] Filed: Oct. 13, 1987

[30] Foreign Application Priority Data

Oct. 16, 1986 [DE] Fed. Rep. of Germany ....... 3635230

[51] Int. Cl.$^4$ ................. C07D 291/00; C07D 211/70; C07D 211/20; C07D 217/10

[52] U.S. Cl. ......................................... 544/2; 546/339; 546/248; 546/102; 546/151; 546/182; 544/109; 544/336; 544/235; 544/283; 544/353; 544/90; 544/105; 544/224; 544/335; 544/392; 544/403; 544/358; 544/88; 544/158; 548/378; 548/574; 548/341; 548/217; 548/241; 548/333; 548/372; 548/215; 548/240; 548/300; 548/356; 558/27

[58] Field of Search .................. 544/2, 109, 336, 224, 544/235, 283, 353, 90, 105, 224, 335, 392, 403, 358, 63, 88, 158; 546/339, 248, 102, 151, 182; 260/501.12; 548/378, 215, 240, 574, 341, 217, 241, 333, 372, 215, 240, 300, 356

[56] References Cited

U.S. PATENT DOCUMENTS 3,320,266  5/1967  Klass ........................................ 544/2

Primary Examiner—Mary C. Lee
Assistant Examiner—Robert C. Whittenbaugh
Attorney, Agent, or Firm—Oblon, Spivak, McClelland, Maier & Neustadt

[57] ABSTRACT

Sulfatobetaines are prepared by reacting an addition compound of sulfur trioxide and a tertiary amine with an alkylene carbonate.

10 Claims, No Drawings

PREPARATION OF SULFATOBETAINES

The present invention relates to a process for the preparation of sulfatobetaines by reacting an addition compound of a base having a tertiary N atom and sulfur trioxide with an alkylene carbonate.

U.S. Pat. No. 3,274,204 describes the preparation of sulfatobetaines by reacting an epoxide with a complex of tertiary amine and sulfur trioxide, by reacting a cyclic sulfate with a tertiary amine or by reacting an epoxide with a complex of dioxane and sulfur trioxide and then reacting the product with a tertiary amine.

The description and the Examples indicate that these processes are advantageously carried out in the presence of an inert solvent, such as toluene, hexane or ethylene dichloride, which may not be completely toxicologically acceptable. Where cyclic sulfates are used as starting materials, they are compounds which are not readily obtainable. Furthermore, we have found that the processes described are not always satisfactory with regard to the yield and purity of the resulting products. If readily volatile epoxides are used, expensive safety precautions are also necessary. The same applies to the process described in German Laid-Open Applications DOS 1,906,851.

German Published Application DAS 1,191,652 states that, for example, pyridinium ethylsulfate (2-pyridinium-1-sulfatoethane) can be prepared in an expensive procedure by reacting hydroxyethylpyridinium chloride, obtained from pyridine and ethylenechlorohydrin, with chlorosulfonic acid. In this procedure too, the yield and purity are unsatisfactory.

It is an object of the present invention to provide a very simple process for the large-scale preparation of sulfatobetaines in high purity and yields.

We have found that this object is achieved by a process for the preparation of sulfatobetaines of the formula I

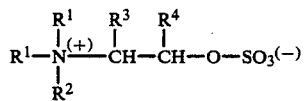

where the individual radicals $R^1$ and $R^2$ may be identical or different and are each a saturated straight-chain or branched alkyl radical of 1 to 22, in particular 1 to 7, carbon atoms, cycloalkyl where the ring is of 5 to 7 carbon atoms, phenyl or naphthyl, or aralkyl having a total of 7 to 12 carbon atoms, and moreover the two radicals $R^1$, together with the N atom, may form a 5-membered or 6-membered heterocyclic ring which may contain one or more further heteroatoms and may contain a fused benzene ring, and $R^2$ is lower alkyl of 1 to 4 carbona atoms, or the two radicals $R^1$, together with the N atom and with $R^2$, form a 5-membered or 6-membered unsaturated heterocyclic ring which may contain one or more further heteroatoms and may contain a fused benzene ring, and $R^3$ and $R^4$ are identical or different and $R^3$ is hydrogen or alkyl of 1 to 7 carbon atoms and $R^4$ is hydrogen, alkyl of 1 to 20 carbon atoms or phenyl, $R^3$ and $R^4$ preferably each being hydrogen or hydrogen and methyl and both radicals being interchangeable with one another, from an addition compound of a base having a tertiary N atom and sulfur trioxide, wherein an amine/SO3 adduct of the formula II

where $R^1$ and $R^2$ have the meanings stated for formula I, is reacted with an alkylene carbonate of the formula III

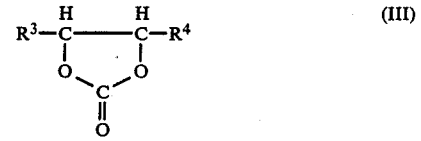

where $R^3$ and $R^4$ have the meanings stated for formula I, at from 80° to 220° C., preferably from 100° to 160° C., in the presence of an excess of the alkylene carbonate of the formula III as a solvent and/or an excess of the base used to prepare the SO3 adduct of the formula II, as a solvent, and/or an inert solvent.

When the novel process is used, sulfatobetaines are obtained in a surprisingly simple manner in high purity and high yields of more than 90%, in conventional stirred kettles, expensive apparatuses being avoided and the handling of highly toxic compounds and solvents being substantially reduced.

In this context, the following may be stated specifically: noteworthy tertiary amines as starting compounds for the amine/SO3 addition compounds of the formula II are tridodecyl-, tristearyl-, tricyclohexyl-, triphenyl-, dimethyldodecyl-, diethylphenyl-, dimethylstearyl-, trimethyl-, triethyl- and tributylamine. The preferred tertiary alkylamines include tertiary amines where the alkyl radicals $R^1$ are each of 1 to 4 carbon atoms and the alkyl radical $R^2$ is of 12 to 18 carbon atoms.

Addition compounds of sulfur trioxide with heterocyclic compounds are particularly preferred. Examples of noteworthy heterocyclic compounds are N-methyl- and N-ethylpiperidine, N-methyl- and N-ethylmorpholine, N-methylpyrazole, oxazole, isooxazole, acridine, phenacridine, pyrazine and pyridazine.

Pyridine which is unsubstituted or substituted by one or two alkyl radicals of 1 to 4 carbon atoms, by carboxyalkyl where alkyl is of 1 to 4 carbon atoms or by nitrile, eg. α-, β- or γ-picoline, 2-ethylpyridine, methyl nicotinate or nicotinonitrile, quinoline or isoquinoline which is unsubstituted or substituted by methyl, such as quinaldine, and N-($C_1$-$C_{12}$-alkyl)-imidazoles which are unsubstituted or substituted on one of the carbon atoms by alkyl of 1 to 6 carbon atoms or phenyl, such as N-methyl- and N-ethylimidazole, 1,2-dimethylimidazole, N-methyl-2-phenylimidazole and 1-dodecylimidazole are particularly preferred.

The SO3 additiion compounds of the formula II can be prepared in a conventional manner or in a reaction mixture as described in the Examples.

The 1,2-alkylene carbonates of the formula III are known in principle and can be prepared, for example, from the corresponding epoxide and carbon dioxide under superatmospheric pressure. It should be pointed out that starting compounds having several cyclic carbonate groups give di- and polysulfatobetaines.

Very particularly preferred starting compounds of the formula III are ethylene carbonate and 1,2-propylene carbonate.

As mentioned above, the reaction of the compound of the formula II with an alkylene carbonate of the formula III is carried out at from 80° to 220° C., preferably from 100° to 160° C., using a molar ratio of the $SO_3$ adduct to the alkylene carbonate of from 1:1 to 1:5, preferably from 1:2.5 to 1:4, the excess cyclic carbonate serving as an advantageous solvent.

It is also possible, particularly when a molar ratio of 1:1 is employed, for the base used to prepare the $SO_3$ addition compound to be employed in excess, as a solvent.

Excess base accelerates the reaction. Because of this effect, it is advisable, regardless of the solvent used, to carry out the reaction according to the invention in the presence of a catalytic amount of the base used to prepare the $SO_3$ addition compound of the formula II. Advantageous amounts are from 0.01 to 10, preferably from 0.1 to 5.0, mol %, based on the $SO_3$ adduct.

It is also possible to use inert solvents, particularly when solid cyclic carbonates of the formula III are employed. Dipolar aprotic solvents, such as dimethylformamide, dimethylpropyleneurea or sulfolane, are advantageous. It is of course also possible to employ mixtures of the solvents used.

Where the addition compound of sulfur trioxide with pyridine is used and is reacted with ethylene carbonate, the reaction according to the invention can be represented by the following equation:

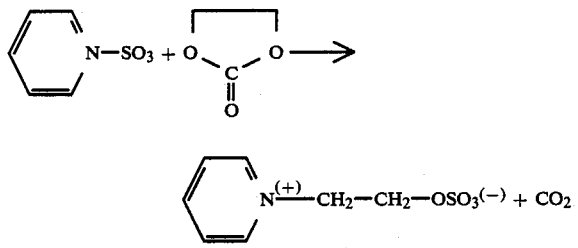

Advantageously, the $SO_3$ addition compound is first prepared in an excess amount of base, in the presence of a solvent or in the presence of the alkylene carbonate, if necessary in excess, at from 40° to 65° C. The actual reaction to give the betaine is then carried out by increasing the temperature to not less than 80° C.

Conversion is complete when $SO_3$ adduct is no longer detectable. In an advantageous procedure, the reaction is terminated by cooling shortly before all the $SO_3$ addition compound has vanished. This avoids discoloration of the solution. Otherwise, the reaction according to the invention can be carried out continuously or batchwise.

The betaines, which are frequently obtained in crystalline form, can be isolated in a simple manner by filtration under suction. After washing with a solvent, such as ethanol or methanol, virtually analytically pure products are obtained.

The compounds prepared by the novel process can be used as surfactants, in particular in detergents or as assistants in the textile sector, as electroplating assistants and as wetting agents, emulsifiers or dispersants.

In particular, heterocyclic ethanosulfates, which are electroplating assistants giving excellent high gloss, are readily obtainable by the novel process. Specific examples of these are pyridiniumsulfatoethane and quinoliniumsulfatoethane.

EXAMPLE 1

261 parts of pyridine and 792 parts of ethylene carbonate were initially taken in a stirred kettle. 240 parts of $SO_3$ were added at 60° C. to prepare the addition compound, after which the temperature was increased to 130° C. Toward the end of the reaction, the pyridiniumsulfatoethane separated out in crystalline form. The suspension was cooled and the crystals were isolated and washed with methanol. The melting point was 203°–205° C. and the yield 92% of theory, based on $SO_3$ used.

Analysis of the resulting crystals without further purification by crystallization showed that the product obtained was analytically pure.

| | Elemental analysis: Molecular weight: 203 | | | |
|---|---|---|---|---|
| | C | H | N | S |
| Calculated | 41.37 | 4.43 | 6.89 | 15.7 |
| Found | 41.3 | 4.5 | 6.9 | 15.5 |

EXAMPLE 2

In order to prepare the $SO_3$ adduct, 237 parts of pyridine were initially taken in a stirred kettle, and 80 parts of $SO_3$ were metered in at 60° C. Thereafter, 88 parts of ethylene carbonate were added dropwise, and the mixture was heated to the boil and stirred under reflux until the reaction was complete. The mixture was cooled, after which the product was filtered off under suction and washed with methanol. Analytically pure crystals of melting point 200° C. were obtained in a yield of 90% of theory, based on $SO_3$ used.

EXAMPLE 3

100 parts of dimethylpropyleneurea, as a solvent, were initially taken together with 40 parts of pyridine. 39 parts of $SO_3$ were metered in at 60° C. to prepare the $SO_3$ addition compound, after which 43 parts of ethylene carbonate were added. The reaction mixture was stirred at 140° C. until the reaction was complete, and then cooled to below 100° C. The product was filtered off under suction and washed with methanol. The resulting crystals of melting point 203° C. were analytically pure and the yield obtained was 89% of theory, based on $SO_3$ used.

The following were prepared according to Example 1 and using the molar ratios employed there:
quinoliniumsulfatoethane of melting point 305° C., in a yield of 90%,
N-methylimidazoliumsulfatoethane of melting point 196° C., in a yield of 90%,
pyridiniumsulfatopropane,
1,2-dimethylimidazoliumsulfatoethane and
3-methylpyridiniumsulfatopropane.

We claim:
1. A process for the preparation of a sulfobetaine of the formula (I):

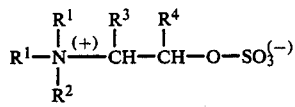

wherein $R^1$ and $R^2$ are the same or different and are each a saturated straight-chain or branched-chain alkyl group of 1 to 22 carbon atoms, cycloalkyl of 5 to 7 carbon atoms, phenyl or naphthyl or aralkyl having 7 to 12 carbon atoms, or $R^1$ and $R^2$, together with the N atom, form a 5- or 6-membered heterocyclic ring, which ring either contains no additional heteroatoms or contains one additional heteroatom selected from the group consisting of nitrogen and oxygen or contains a fused benzene ring; $R^3$ and $R^4$ are the same or different and $R^3$ is hydrogen or an alkyl group of 1 to 7 carbon atoms and $R^4$ is hydrogen, an alkyl group of 1 to 20 carbon atoms, or phenyl, which process comprises:

reacting an addition compound of a base having a tertiary N atom and sulfur trioxide having the formula (II):

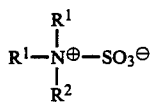

wherein $R^1$ and $R^2$ are as defined above with an alkylene carbonate of the formula (III):

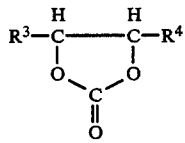

wherein $R^3$ and $R^4$ are as defined above, and from 80° to 220° C. in the presence of an excess of the alkylene carbonate, as a solvent, and an excess of the base used to prepare the sulfur trioxide adduct, as a solvent, in an amount sufficient to also accelerate said reaction.

2. The process as claimed in claim 1, wherein a heterocyclic addition compound of sulfur trioxide with pyridine, which is unsubstituted or substituted by one or two alkyl radicals of 1 to 4 carbon atoms, by carboxyalkyl where alkyl is of 1 to 4 carbon atoms or by nitrile, with quinoline or isoquinoline, which is unsubstituted or substituted by methyl, or with an N-($C_1$–$C_{12}$-alkyl)-imidazole, which is unsubstituted or substituted at one of the carbon atoms by alkyl of 1 to 6 carbon atoms or by phenyl, is used.

3. The process as claimed in claim 1, wherein the cyclic carbonate used is ethylene carbonate or 1,2-propylene carbonate.

4. The process as claimed in claim 1, wherein the reaction is carried out in the presence of from 0.01 to 10 mol %, based on the $SO_3$ addition compound, of the base used to prepare the $SO_3$ addition compound.

5. The process as claimed in claim 1, wherein the addition compound of sulfur trioxide with pyridine is reacted with ethylene carbonate.

6. The process as claimed in claim 1, wherein the reaction of said addition compound and said alkylene carbonate is conducted at a temperature of 100° to 160° C.

7. The process of claim 1, wherein in said addition compound of a base having a tertiary N atom and sulfur trioxide, $R^1$ is a $C_1$–$C_4$ alkyl group, and $R^2$ is a $C_{12}$–$C_{18}$ group.

8. The process as claimed in claim 1, wherein $R^1$ and $R^2$ form a heterocyclic ring, which is N-methyl- and N-ethyl-piperidine, N-methyl- and N-ethyl-morpholine, N-methylpyrazole, oxazole, isooxazole, acridine, phenacridine, pyrazine and pyridazine.

9. The process as claimed in claim 1, wherein a molar ratio of $SO_3$ adduct to alkylene carbonate of from 1:1 to 1:5 is used.

10. The process as claimed in claim 9, wherein said molar ratio is from 1:2.5 to 1:4.

* * * * *